United States Patent [19]

Bellis

[11] Patent Number: 5,696,287
[45] Date of Patent: Dec. 9, 1997

[54] PROCESS FOR MAKING AQUEOUS BETAINE SOLUTIONS

[75] Inventor: Harold Edward Bellis, Wilmington, Del.

[73] Assignee: DuCoa, L. P., Highland, Ill.

[21] Appl. No.: 681,033

[22] Filed: Jul. 22, 1996

[51] Int. Cl.$^6$ ............................................. C07C 229/00
[52] U.S. Cl. .................................................... 562/575
[58] Field of Search ........................................ 562/575

[56] References Cited

U.S. PATENT DOCUMENTS 2,800,502  7/1957  Vassel ................................. 562/575
5,292,942  3/1994  Aigner ................................ 562/575
5,371,250  12/1994  Seitz ................................. 562/575

FOREIGN PATENT DOCUMENTS

PI 9301144-A  1/1994  Brazil.

Primary Examiner—Michael L. Shippen

[57] ABSTRACT

Process for producing high purity aqueous solutions of betaine by reaction of substantially equal molar ratios of trimethylamine and an alkaline salt of monochloroacetic acid in aqueous solution.

8 Claims, No Drawings

PROCESS FOR MAKING AQUEOUS BETAINE SOLUTIONS

FIELD OF THE INVENTION

The invention is directed to a synthetic process for making aqueous solutions of betaine. In particular, it is directed to such a process in which the betaine product is especially adapted for use in animal feed applications.

BACKGROUND OF THE INVENTION

Betaine is a well-known product which has been used widely in a number of applications for many years. Until recently, betaine was used mainly in cosmetics, fish food and as a supplement in food for humans. Recently, new uses of betaine have been investigated, especially incorporation of betaine into feed for swine and poultry. Consistent with a current trend to decrease the amount of human fat intake, the primary use in swine feed is centered around effectiveness of betaine to decrease the amount of backfat on finishing pigs. In addition there is considerable interest in the effectiveness of betaine as a cellular osmotic regulator. In this application, betaine improves the functionality and integrity of intestinal cell walls by which nutrient absorption and animal health are improved and dehydration is limited.

Heretofore, most of the betaine has been derived from natural sources such as beet molasses. Natural sources of betaine are, however, limited and are insufficient to meet the prospective demands for the product. Several synthetic routes to the production of betaine have been proposed. For example, Brazilian patent PI 9301144-0 A, which is the closest prior art of which applicant is aware, is directed to making an animal feed supplement comprising betaine and wheat bran. The betaine is produced by reaction of sodium monochloroacetate, trimethyl ammonium chloride and sodium hydroxide in aqueous solution. The pH of the reaction mixture is adjusted with HCl, after which it is concentrated to precipitate NaCl, which is removed from the reaction mixture by filtration. This process is technologically feasible, but the product is isolated as a crystalline solid along with substantial quantities of trimethyl amine hydrochloride and unreacted sodium monochloroacetate.

Therefore, in contemplation of the increasing demand for betaine throughout the world, there remains a substantial need for a synthetic route to the production of betaine which is both economically viable for large scale production and has higher purity betaine suitable for human food applications.

SUMMARY OF THE INVENTION

In its primary aspect, the invention is directed to a method for the synthesis of high purity aqueous solutions of betaine comprising the steps:

(1) forming an aqueous solution of trimethyl amine and an alkali metal salt or alkaline earth metal salt of monochloroacetic acid in which the molar ratio of trimethyl amine to the chloroacetic acid salt is 1.0 to 1.1;

(2) with continuous agitation, reacting the trimethyl amine with the monochloroacetic acid salt, while maintaining the pH of the reaction mixture at a level no higher than 9, and maintaining the temperature of the reaction mixture at 40–90 C. for a time sufficient to effect essentially complete reaction of the monochloroacetic acid salt in the reaction mixture by which betaine and alkali metal chloride or alkaline earth metal chloride are formed and dissolved in the reaction mixture;

(3) removing any residual amount of monochloroacetic acid and homologous contaminants thereof contained in the reaction mixture to a level no higher than 10 ppm by weight; and (4) removing any unreacted trimethyl amine contained in the reaction mixture to a level no higher than 10 ppm by weight.

DETAILED DESCRIPTION OF THE INVENTION

The first step of the invention is directed to the preparation of an aqueous solution of an alkaline salt of monochloroacetic acid (MCAA). In this step, the salt is prepared by reaction of an alkali with the MCAA. The solution can be prepared by addition of the MCAA to the alkaline solution or vice versa. The hydroxides of either alkali metals or alkaline earth metals can be used for this purpose. However, alkali metal hydroxides are preferred and sodium and potassium hydroxides are particularly preferred. The needed amount of alkali metal or alkaline earth metal hydroxides, including mixtures thereof, is controlled by the pH of the reaction solution. That is, in order to get good yields of betaine, it is preferred that the alkalinity of the reaction solution not exceed pH 7. A pH level of 5.5–7 is preferred during caustic addition. Cooling should be applied during caustic addition to maintain the temperature at a temperature no higher than 40 C. It is further preferred that the caustic be added as a 30% wt. or lower solution to lessen local heating and hydrolysis of the chloroacetic acid.

The second step of the invention process is addition of TMA to effect essentially complete reaction of the MCAA. As used herein, the term "essentially complete reaction" means that the amount of residual unreacted MCAA does not exceed about 1,000 ppm by weight, basis total weight of the reaction solution.

When carrying out the addition of TMA to MCAA during practice of the invention, the molar ratio of TMA to MCAA should be approximately 1.0 and in no event should exceed 1.1. The TMA/MCAA ratio should not be less than 1.0 in order to avoid excessive amounts of MCAA in the reaction mixture upon completion of TMA addition. It is preferred to use a slight molar excess of TMA, e.g., 1.05–1.10, in order to minimize the presence of various MCAA-derived impurities in the reaction product. If the molar ratio of TMA exceeds about 1.1, the pH of the reaction rises and excessive mounts of glycolic acid impurities are formed thereby.

The temperature of the reaction during TMA addition is not particularly critical, but will ordinarily be 40–90 C. Within this range of temperature, reaction rates are satisfactory and neither decomposition nor evaporation of the reactants is significant. It is preferred that the reaction temperature not exceed about 90 C. in order to avoid hydrolysis of the MCAA. A reaction temperature of 50–60 C. is still further preferred. In carrying out the process of the invention, it is preferred that the TMA be added as a gas.

The rate of addition of reaction materials throughout the process is preferably carried out at a level such that severe exotherms are avoided. In the case of TMA addition, it is preferred that the reaction temperature be kept low in order to lessen the evaporation of the TMA from the reaction mixture.

Upon completion of the TMA addition and its reaction with the alkaline MCAA salt, it will usually be preferred to remove impurities from the reaction mixture. An effective way of doing this is to heat the reaction mixture with the addition of alkali metal hydroxide to raise the pH of the mixture to at least 10. This procedure hydrolyses any unreacted MCAA and any TMA salts, e.g., the HCl, which may have formed. It is not usually necessary to remove these hydrolysates from the reaction mixture. However, if desired, such MCAA-related contaminants can be removed by ion exchange. This latter method, either alone or in combination with the caustic treatment, is preferred when it is desired to reduce the level of MCAA-related contaminants substantially below 10 ppm.

Unreacted TMA contained in the reaction solution is most easily removed by stripping. The stripping operation is preferably carried out using an inert gas in order to avoid oxidation of the betaine product. The stripping may be carried out under vacuum or pressure. Suitable stripping media include steam and inert gases such as nitrogen. It is further preferred to conduct the stripping operation under anaerobic conditions. By the exclusion of sources of free oxygen, there will be less generation of colored species, especially those derived from the amines. Vacuum stripping using nitrogen gas has been found to be a very efficient way of stripping of TMA from the aqueous reaction mixture, preferably after the pH has been raised to at least 10. Solutions of betaine made in the foregoing manner can be freeze-dried or spray-dried to form solids exhibiting good resistance to humidity.

EXAMPLES

Examples 1–8

A series of eight tests was run to observe the effect of pH in the second step of the invention. In the first of the eight tests, 830 g of an aqueous solution of 29% wt. NaOH was added at atmospheric pressure to a 2 liter glass stirred reactor containing 708 g of an aqueous solution of 80% wt. monochloroacetic acid (MCAA) over an interval of about 1.4 hours. The solution had a pH of 4. Upon completion of the NaOH addition, 353 g of anhydrous trimethylamine (TMA) was added to the alkaline solution of chloroacetic acid over an interval of about 4.4 hours. The temperature during the latter reaction step was 45 C., and the pH rose from about 8.5 to 10.9. The molar ratio of TMA/MCAA was 1.02. Upon completion of the TMA addition, the betaine content of the solution was analyzed. Further tests were carried out in the same manner except that the pH was changed to various levels by changing the amount of NaOH added to the MCAA and the temperature was varied. The results of this series of tests are given in Table 1 below.

TABLE 1

Effect of pH on Betaine Yields

| Ex. No. | pH | Temperature (C.) | Betaine Yield (% wt.) |
| --- | --- | --- | --- |
| 1 | 10.9 | 45 | 55 |
| 2 | 11.2 | 65 | 40 |
| 3 | 9.2 | 55 | 98 Buffered |
| 4 | 8.7 | 45 | 100 |
| 5 | 8.5 | 65 | 98 |
| 6 | 8.8 | 55 | 98 Buffered |
| 7 | 10.2 | 55 | 64 |
| 8 | 9.2 | 55 | 92 |

The foregoing data show that within the temperature range of 45–65 C., the yield of betaine can be maximized by operation at an unbuffered pH no higher than 9. The data also indicate that within the 45–65 C. temperature range, variations in temperature are not particularly critical.

Example 9

A larger scale synthesis of betaine was carried out in a stirred 120 gallon (454 L) stainless steel reactor. The proportions of the reactants were as follows: 169.5 lbs. (76.9 kg) anhydrous TMA, 273 lbs. (123.8 kg) MCAA, 117 lbs. (53.1 kg) NaOH and 441 lbs. (200.0 kg) water.

The solid crystalline MCAA was added to the water over a period of 25 minutes, after which aqueous NaOH was added to effect neutralization of the MCAA. The aqueous NaOH solution, which contained 273 lbs. (123.8 kg) H2O and 117 lbs. (53.1 kg) NaOH, was added over a period of about 55 minutes to reach a final pH of 5.8. Upon completion of the caustic addition, vaporous anhydrous TMA was added to the neutralized MCAA solution over a period of about 4.5 hours. Reaction temperature rose from 40 C. to about 52 C. during the first hour of TMA addition and stayed at about the same temperature during the next 3 hours. At the conclusion of TMA addition, the reaction temperature was lowered to 50 C. During the TMA addition, it was noted that the pressure within the reactor did not rise significantly until the very end of the TMA addition. This indicates that the reaction of the TMA with the MCAA was very rapid throughout the addition period until substantially all the MCAA was reacted. Upon completion of the TMA addition, the reaction solution was stripped with N2 gas to strip out unreacted TMA. The reactor head space contained 426 ppm by weight of the TMA upon completion of the TMA addition, but contained only 10 ppm TMA after stripping with nitrogen gas. The overall process time, including sampling, was 13.25 hours. Betaine yield was 97% wt. (969 lbs., 440 kg).

I claim:

1. A process for producing aqueous betaine solutions comprising the steps:

(1) forming an aqueous solution of trimethyl mine and an alkali metal salt or alkaline earth metal salt of monochloroacetic acid in which the molar ratio of trimethyl amine to the chloroacetic acid salt is 1.0 to 1.1;

(2) with continuous agitation, reacting the trimethyl amine with the monochloroacetic acid salt while maintaining the pH of the reaction mixture at a level no higher than 9 and maintaining the temperature of the reaction mixture at a temperature of 40–90 C. for a time sufficient to effect essentially complete reaction of the monochloroacetic acid salt in the reaction mixture by which betaine and an alkali metal chloride or alkaline earth metal chloride are formed and dissolved in the reaction mixture;

(3) removing any residual amount of monochloroacetic acid and homologous contaminants thereof contained in the reaction mixture to a level no higher than 10 ppm by weight; and (4) removing any trimethyl amine contained in the reaction mixture to a level no higher than 10 ppm by weight.

2. The process of claim 1 in which the monochloroacetic acid salt is the sodium salt of monochloroacetic acid.

3. The process of claim 1 in which the monochloroacetic acid salt is formed by reaction of monochloroacetic acid with an alkali metal or alkaline earth metal hydroxide in aqueous solution and step (1) is carried out by addition of the trimethyl amine to the solution of the salt.

4. The process of claim 1 in which residual monochloroacetic acid is removed from the reaction mixture by addition thereto of sodium or potassium hydroxide at a temperature of 50–90 C. to raise the pH to at least 10 by which the monochloroacetic acid is hydrolyzed.

5. The process of claim 1 in which residual trimethyl amine is removed from the reaction mixture by stripping with a vapor under anaerobic conditions.

6. The process of claim 5 in which the reaction mixture is stripped under vacuum with nitrogen gas.

7. The process of claim 6 in which the pH of the reaction mixture is adjusted to at least 10.

8. The process of claim 1 in which the temperature during step (2) is 50–60 C.

* * * * *